United States Patent
Savrasov et al.

(10) Patent No.: US 6,905,473 B2
(45) Date of Patent: Jun. 14, 2005

(54) METHOD AND DEVICE FOR THERAPY OF BIOLOGICAL TISSUES USING AN ULTRASONIC FIELD

(75) Inventors: Gennady Victorovich Savrasov, Moscow (RU); Oleg Stepanovich Naraikin, ul. 26 Bakinskikh Komissarov., 6-22-115, Moscow (RU), 117526

(73) Assignees: Olga Pavlovna Barysheva, Moscow (RU); Oleg Stepanovich Naraikin, Moscow (RU); Victor Frunzevich Tarkhov, Moscow (RU); Sergei Frunzevich Tarkhov, Moscow (RU)

(*) Notice: Subject to any disclaimer, the term of this patent is extended or adjusted under 35 U.S.C. 154(b) by 104 days.

(21) Appl. No.: 10/169,522
(22) PCT Filed: Feb. 22, 2001
(86) PCT No.: PCT/RU01/00076
§ 371 (c)(1), (2), (4) Date: Jul. 2, 2002
(87) PCT Pub. No.: WO02/04074
PCT Pub. Date: Jan. 17, 2002

(65) Prior Publication Data
US 2002/0188230 A1 Dec. 12, 2002

(30) Foreign Application Priority Data
Jul. 10, 2000 (RU) .................................... 2000118669

(51) Int. Cl.[7] .............................................. A61B 17/22
(52) U.S. Cl. ........................................................ 601/3

(58) Field of Search ......................... 601/2–4; 604/22, 604/890.1, 891.1, 892.1; 606/1; 600/439

(56) References Cited

U.S. PATENT DOCUMENTS

| 4,315,514 A | * | 2/1982 | Drewes et al. ............... 600/427 |
| 5,618,275 A | * | 4/1997 | Bock ........................... 604/290 |
| 5,735,811 A | * | 4/1998 | Brisken ........................ 604/22 |
| 5,814,599 A | * | 9/1998 | Mitragotri et al. ............. 514/3 |
| 6,096,000 A | * | 8/2000 | Tachibana et al. ............ 604/20 |

\* cited by examiner

Primary Examiner—Francis J. Jaworski
(74) Attorney, Agent, or Firm—Garrison & Associates PS; David L. Garrison

(57) ABSTRACT

The invention relates to the art of medicine and medicine equipment and concerns techniques and means for therapeutic action to biological tissues with electromagnetic fields. The invention allows to improve the therapeutic effectiveness of action with ultrasonic fields to biological tissue. The action is effected with the ultrasonic fields having frequencies corresponding to intrinsic frequencies of mechanical oscillations a cell membrane (that is, to resonance frequencies). The action to the cell membranes is effected in a hydrodynamic non-destructive mode. A device for therapeutic action with a ultrasonic field to biological tissues comprises a ultrasonic oscillation generator, an acoustic assembly and a ultrasonic tool that is a replaceable operating member having an operating end, and further has a liquid phase supply system. The generator is capable of forming the ultrasonic field having a frequency of from 20 to 30 kHz. A form of the operating end of the ultrasonic tool corresponds to a form of a receiving surface of a biological tissue, and is described by cubic splines.

4 Claims, 2 Drawing Sheets

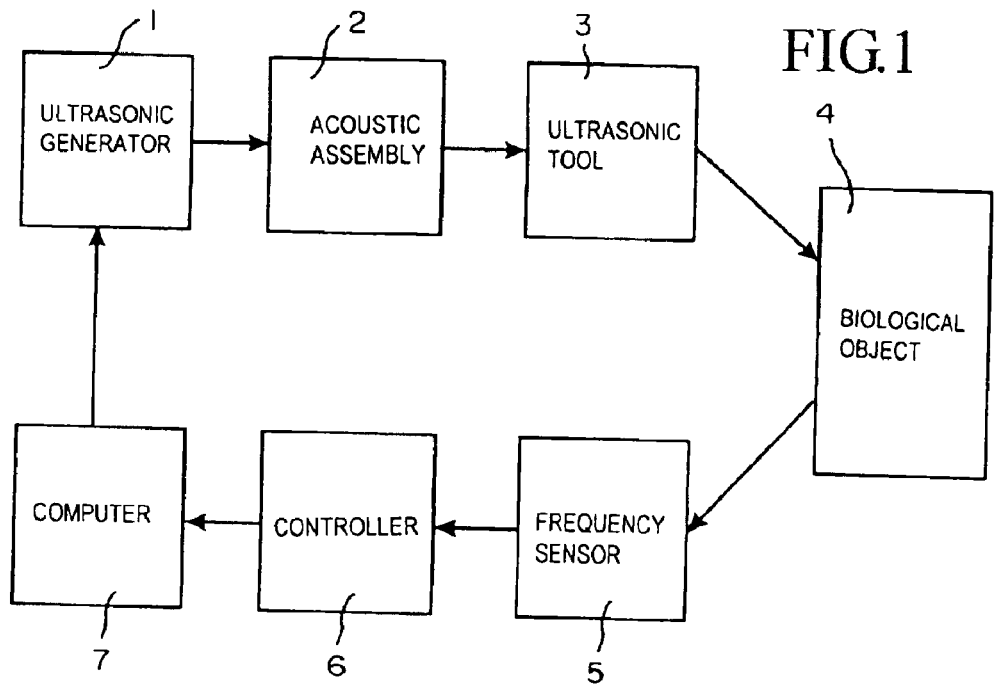
FIG.1
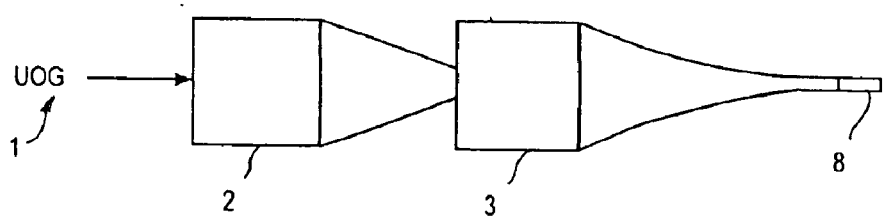
FIG.2
FIG.3
FIG.4
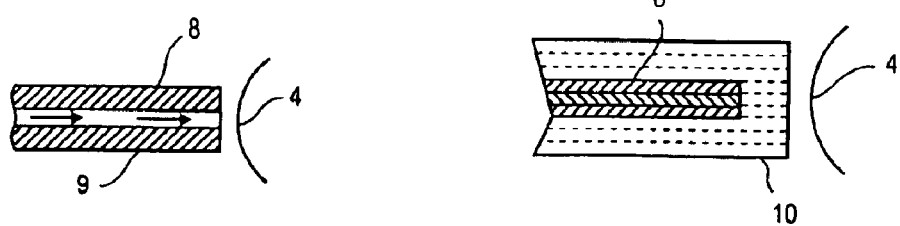

METHOD AND DEVICE FOR THERAPY OF BIOLOGICAL TISSUES USING AN ULTRASONIC FIELD

TECHNICAL FIELD

This invention relates predominantly to the art of medicine and medicine equipment and concerns techniques and means of therapeutic action to biological tissues with ultrasonic fields. It also can be used in veterinary and during scientific biological studies.

BACKGROUND ART

In modern medicine, methods associated with use of ultrasonic fields have found application in surgical practice, diagnostic investigations, therapeutic procedures.

With the assistance of ultrasound, liquids and surgical instruments are sterilised, high-dispersion forms of medicinal preparations are prepared.

Depending upon characteristics of ultrasonic fields, the last-mentioned can cause a wide diversity of physical effects in systems subjected to processing, exactly, mechanical destruction, dispersion, emulsification, cavitation, thermal heating, excitation of intrinsic oscillations, etc. (Ultrazvuk. Malenkaya Entsiklopedia (Ultrasound. Small Encyclopaedia)./Ed. by I.P. Golyamina. Moscow: Sovetskaya entsiklopedia (Soviet Encyclopaedia Publishers). 1979.-399 pp.).

When ultrasonic fields having different characteristics act to biological tissues, complexes of active physics factors can imply an antiphlogistic, anaesthetic, disinfecting, stimulating action.

To treat urolithiasis, for example, it has been proposed to act to the region of the projection of kidneys with opposite phase ultrasonic fields simultaneously from back and abdomen in the plane of location of a kidney, said fields having a frequency of from 1 to 5 kHz and an intensity of from 2 to 5 mW/cm$^2$, wherein selection of the frequency and intensity is carried out according to subjective perceptions of a patient.

The opposite phase operation of radiation sources provides not merely increase of an intensity of oscillations but achievement of its more uniform distribution in a patient's body in the travelling wave mode with the constancy of an intensity of action within a resonator formed by the patient's body (RF Patent 2,099,040, A 61 H 23/00, 1997).

The prior art method for treatment of children having chronic pyelonephritis comprises the step of acting to the region of kidneys, adrenal glands and urhetrae with a ultrasonic field having a frequency of 880 kHz at an intensity of from 0.05 to 0.2 W/cm$^2$, the intensity and duration of action being increased depending upon the severity of a disease.

In such modes of action with ultrasonic fields, the stabilising effect is achieved relative to cell membranes of kidneys, that allows to reduce treatment periods and to decrease the number of exacerbations (USSR Inventor's Certificate 1,456,153, A 61 H 23/00, 1989).

To prevent the second-order reactions of regional hemodynamics when the vibration massage is carried out, there are the steps of preliminary determining the second harmonic of an intrinsic frequency of a patient's cardiovascular system on the basis of rheographic data obtained after applying a series of actions with frequencies of from 16 to 32 Hz with a step of 2 Hz, an amplitude of 4 mm, a duration of 2 minutes from an extremity by a peak of an average velocity of the maximum pulse volume, and effecting a vibration action at said frequency (USSR Inventor's Certificate 1,163,853, A 61 H 23/00, 1985).

When mechanical vibration actions are effected for stimulating the muscles of sportsmen, there are the steps of preliminary measuring a frequency and an amplitude of mechanical oscillations generated by tensioned muscles, and effecting a vibration action at a frequency being a multiple of the measured frequency, and with an amplitude being equal to the measured amplitude (USSR Inventor's Certificate 1,174,026, A 61 H 23/00, 1985).

Disclosure has been made of a device for ultrasonic therapy, whose function basis was the principle of synchronising a ultrasonic action with a frequency, an amplitude and a duration of a determined biological parameter, for example, a blood volume of a body section to be irradiated. In doing so, information about some biological parameter, for example a frequency, an amplitude and a duration of pulse oscillations, is converted into an electrical signal that, after amplification and filtration, guides the operation of the generator.

Such a constant biocontrol and bioregulation by ultrasonic fields allows to individualise and optimise the character of action (USSR Inventor's Certificate 562,279, A 61 H 23/00, 1977).

The similar method of action of ultrasonic fields to animal organisms comprises the steps of fixing a primary information sensor (for example, a piezoelectric sensor) at a body of an animal, which sensor controls the operation of a ultrasonic oscillation generator. As a primary information it is possible to use, for example, information about a pulse rate. An electrical signal in the form of a sine-like curve obtained from the primary information sensor is supplied as a control signal to the ultrasonic oscillation generator.

Thus, the action with a ultrasonic field is effected at a periodicity equal to a contraction frequency of the cardiovascular system of an organism, that reduces the energy supply to the organism because tissues, especially a nervous tissue, are more responsive to intermittent irritations than to continuous irritations (USSR Inventor's Certificate 649,429, A 61 H 23/00, 1979).

It has been patented a ultrasonic therapeutic apparatus whose design aspects allow to create a stochastic and wideband ultrasonic field, that has certain advantages: the action of said fields does not cause the habituation and reduces the second-order actions to tissues surrounding an affection nidus, because the acoustic energy is distributed in a wide frequency range.

This apparatus includes a ultrasonic oscillation source comprising a signal frequency and phase variator, a power amplifier comprising an amplitude normaliser, wherein the power amplifier is connected to a wideband ultrasonic radiator in the form of a multimode cavity resonator, said radiator being polarised according to a linear law (RF Patent 2,066,215, A 61 H 7/00, 1996).

As the effectiveness of action of ultrasonic fields to an organism is determined by parameters of a used ultrasonic field and modes of action, then, selection of said parameters is of critical importance.

In all the above-mentioned techniques of action of ultrasonic fields to an organism, the parameters of an active field were determined empirically or were based on values defining the activity of a patient's cardiovascular or muscular system.

However, the selection of active ultrasonic field parameters according to said criteria has no clear biophysical basis, and there is no any assurance that such parameters are optimal.

BRIEF DISCLOSURE OF INVENTION

The Applicant was the first to establish that, in action to a living cell with ultrasonic fields in a hydrodynamic, membrane-non-destructive mode at frequencies being coincident with that of intrinsic mechanical oscillations of a cell membrane (that is, with resonance frequencies of the cell membrane), the increase of the cell membrane permeability takes place, that can be taken as a basis for improvement of modem methods of treatment.

The aim of the present invention consists in increasing the therapeutic effectiveness of action of ultrasonic fields to biological tissues.

To achieve this aim and to restore functions of a biological tissue subjected to pathological changes, said tissue is acted with a ultrasonic field having a frequency corresponding to a frequency of intrinsic mechanical oscillations of a cell membrane of a respective biological tissue, and said actions are effected in a non-destructive hydrodynamic mode.

The Applicant has found that the values of the lowest found intrinsic frequency mechanical oscillations of healthy cell membranes in the majority of soft tissues are in the range of from 23 to 27 kHz."

To implement the inventive method, an external ultrasonic field frequency should correspond to the lowest found intrinsic frequency of mechanical oscillations of a cell membrane.

Other important characteristic of the inventive method is an intensity of an active ultrasonic field, that should be essentially lower than a level having effect on a destructive action to cell membrane.

The Applicant assumes that an average intensity of an active resonance ultrasonic field should be within from 0.2 to 0.5 mW/cm$^2$.

Another condition to implement the inventive method is the necessity of its realisation in a hydrodynamic mode, because a liquid medium can serve as a carrier of ions and substances to be delivered into a cell, or can assist in removal of undesirable ions and substances from the cell.

Being a translator of ultrasonic energy, a liquid medium, depending upon its physical and chemical characteristics, can weak or amplify an intensity of a ultrasonic field that it receives.

A hydrodynamic mode of action can be provided by use of water, aqueous and salt solutions, mineral and vegetable oils, aqueous suspensions or emulsions, gels or colloid systems as a liquid medium.

The inventive method can be used for treatment of inflammatory diseases of skin integument, traumatic injuries, burns, in otolaryngology, in gynaecology, in proctology.

To practise the inventive method, it is possible to use a device comprising at least a ultrasonic oscillation generator capable of forming a field having a frequency of from 20 to 30 kHz, a liquid phase transmission system that provides a hydrodynamic operation mode, and an operating member creating a uniform ultrasonic field evenly acting to a biological material.

However, preference is given to automated devices equipped with respective additional means.

The essential and specific feature of the device necessary to implement the inventive method is a design form of a radiating surface of the operating member.

As a result of the performed search work, the Applicant has shown that it is possible to achieve sufficient results if a form of the radiating surface of the operating member is designed by a spline approximation method, because it is only and precisely the case when the necessary degree of similarity for radiating and receiving surfaces can be achieved.

In practice, as found during the Applicant's studies, thought as satisfactory may be a degree of similarity that can provide the scatter of energy concentrations within 30% at a receiving surface.

Calculations lead to the conclusion that an optimum form of a radiating surface should have a curvature corresponding to that of the receiving surface.

In particular, it was shown that, to irradiate internal surfaces of tubular organs, for example of rectum, it is desirable to have an ellipsoid form of the radiating surface of the operating body; therefore, the operating member having the radiating surface of ellipsoid form can be effectively and successively used in proctologic practice; in gynaecology, it is best to use an operating member having a radiating surface that is made as a cylinder having a skewed end face portion; in otolaryngology, it is best to use an operating member having a radiating surface that is made as a concave bowl.

The radiating surface of the operating member is localised at its end that directly contacts a biological tissue.

Of course, said forms do not limit the assortment of operating members intended to solve different particular problems, and a form of their radiating surfaces can be designed on the basis of the principles stated above.

BRIEF DESCRIPTION OF THE DRAWING

FIG. 1 is a block diagram of the present invention.

FIG. 2 is a structural diagram of the present invention.

FIG. 3 is a cross-sectional view of one embodiment of the operating end of the present invention shown in relationship to the zone of action.

FIG. 4 is a cross-sectional view of a second embodiment of the operating end of the present invention shown in relationship to the zone of action.

DETAILED DISCLOSURE OF INVENTION

Figure 5:
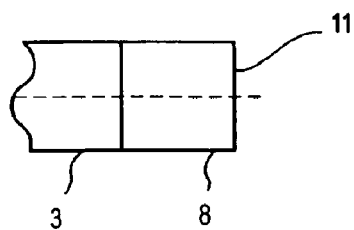
FIG. 5 is a cross-sectional view of a third embodiment of the operating end of the present invention shown in relationship to the zone of action.

The scientific fact first established by the Applicant was placed as the basis of invention, said fact consisting in that, when a living cell is acted in a membrane-non-destructive hydrodynamic mode with ultrasonic fields having frequencies coincident with that of intrinsic mechanical oscillation of a cell membrane, that is, with resonance frequencies of the cell membrane, the decrease of a permeability of the cell membrane takes place, that is probably associated with opening of so called "ion channels" through which substrate and metabolite ions and molecules are transported into and out of the cell.

The establishment of said fact allows to have a purposeful effect to supply of necessary ions, energy substrates and medicinal substances into a cell, and/or provision of evacuation of toxic substances and (or) metabolites out of the cell, depending upon modes of supersonic action.

In medical practice, this phenomenon can be used to restore and maintain normal conditions of full-value functioning of a living cell disturbed as a result of pathological processes.

The main aim of the present invention consists in improvement of action of ultrasonic fields to biological tissues, that particularly can result in the following:

widening functional abilities of use of ultrasound fields as an active medicinal factor in medicine and the adjacent art;

widening the arsenal of means capable of effecting to an intensity of exchange processes in a cell;

appearing the real ability of direct activating the supply of necessary substrates, including medicinal substances, into a cell, or evacuating undesirable products, including toxic, out of the cell.

The posed aim is achieved due to use of ultrasonic fields having frequencies corresponding to that of intrinsic mechanical oscillations of a cell membrane (that is, to resonance frequencies), whose action is effected in a hydrodynamic non-destructive mode.

The achievable physical effect consists in increasing the permeability of a cell membrane as a result of opening "ion channels", that facilitates the transmembranous transportation of ions and molecules.

The essence of the Applicant's proposal is as follows.

A biological tissue subjected to pathological changes is acted, to restore its disturbed functions, with a ultrasonic field having a frequency being coincident with that of intrinsic mechanical oscillations of a cellular membrane of a respective tissue, and said actions are effected in a non-destructive hydrodynamic mode.

Mechanical oscillation frequency values of cell membranes of biological tissues can be determined experimentally by prior art methods or obtained by calculation in a known manner, it is also possible to use available literature data.

For example, the Applicant has found that values of the lowest found intrinsic frequency of mechanical oscillations of healthy cell membranes for the majority of soft tissues are within an interval of from 23 to 27 kHz.

Particular values of the cell membrane mechanical oscillation frequencies depend upon an age of cells, their physical and chemical nature, and upon other reasons.

To implement the inventive method, a frequency of an external ultrasonic field should correspond to the lowest found intrinsic frequency of mechanical oscillations of a cell membrane.

Usually, it is quite sufficient if a frequency of a ultrasonic field corresponds to one of intrinsic frequencies of a membrane.

Principally, a frequency of an active ultrasonic field can correspond to any intrinsic frequency of cell membrane oscillations, but it is more preferable to form the most low-frequency ultrasonic fields, that requires smaller energy consumption.

At the same time, a frequency of an active ultrasonic field can be constant (if a frequency of mechanical oscillations of a cell membrane is not know with a sufficient accuracy) or be set within a range of values (if a frequency of mechanical oscillations of a cell membrane is know with a sufficient accuracy) to achieve the guaranteed resonance effect.

Another important characteristic of the inventive method is an intensity of an active ultrasonic field, that should be significantly lower than a level causing a destructive action to a cell membrane.

Therefore, an intensity of an active ultrasonic field used to implement the inventive method should be a priori lower than said value.

At the same time, we have to take into account the circumstance that an active ultrasonic field is capable of causing resonance oscillations of a cell membrane, for which reason an intensity of the ultrasonic field should be several orders lower than the destruction energy for the membrane.

Taking the foregoing into account, an optimum intensity of an active resonance ultrasonic field should be within from 0.2 to 0.5 mW/cm$^2$.

Another condition to implement the inventive method is the necessity to realise said method in a hydrodynamic mode.

The last-mentioned is associated with that a liquid medium receiving the ultrasonic actions becomes a necessary attribute of the method: when penetrating into a living cell, said medium can serve as a carrier of ions or substances to be delivered into the cell, or, when evacuating out of the cell, said medium can serve as an agent removing undesirable ions and substances from the cell.

Additionally, it is the liquid medium that provides a hydrodynamic mode of ultrasonic action, is itself subjected to ultrasonic actions whose energy the medium translates directly to a biological tissue, thereby causing respective energy effects.

Being a translator of ultrasonic energy, a liquid medium, depending upon its physical and chemical characteristics, can weak or amplify an intensity of a ultrasonic field that it receives.

A hydrodynamic mode of action can be provided by use of water, aqueous and salt solutions, mineral and vegetable oils, aqueous suspensions or emulsions, gels or colloid systems as a liquid medium.

The inventive method can be successively used for treatment of inflammatory diseases of skin integument, traumatic injuries, burns, in otolaryngology, in gynaecology, in proctology.

The essential and specific feature of the device necessary to implement the inventive method is a design form of a radiating surface of an operating member.

The radiating surface of the operating member is localised at its end that directly contacts a biological tissue.

Since according to the inventive method a therapeutic action with ultrasonic fields is effected by fields of low energies, the uniformity of action to the entire surface of a biological tissue is of a special importance. The non-uniformity of actions or non-uniformity of an active field can result in that a lower field intensity at some sections of the biological tissue can be not able to provide a necessary biological effect, and a higher field intensity at other sections can cause the achievement of a surplus effect.

The situation is aggravated by the fact that surfaces of biological tissues which can be acted with ultrasonic fields, have different configuration and curvature, because medicinal actions can be effected to different sections of a skin surface, to internal organs of different forms and dimensions, and to their surfaces.

Selection of a form of a radiating surface of an operating member, that allows to increase the degree of action uniformity, is an independent creative problem.

As a result of performed search work, the Applicant has shown that satisfactory results can be achieved if a form of a radiating surface is designed by the spline approximation method, because it is only and precisely the case when the necessary degree of similarity for radiating and receiving surfaces can be achieved.

Such a conclusion was made from the following theoretic prerequisites.

When the radiating and receiving surfaces are completely similar, the concentration of ultrasonic energy at each section of the receiving surface should be the same.

In this case, the concept "similarity of radiating and receiving surfaces" means the adequacy of configuration, relief and curvature of said surfaces.

Such a degree of similarity, however, is ideal because said degree is difficult to be provided, and practically, as found during the Applicant's studies, thought as satisfactory may be a degree of similarity that can provide the scatter of energy concentrations within 30% at a receiving surface.

In this connection, experimental studies are necessary to select an approximation method using cubic splines and allowing to describe a form of a radiating surface to such a degree of similarity of the radiating surface, that could be able to provide a satisfactory uniformity of a ultrasonic energy field that achieves an irradiated surface.

Finally, it was found that the searched result can be obtained only in use of the spline approximation method, and use of other means, particularly Lagrange polynomials or Chebyshev polynomials, does not allow to design a form of a radiating surface, that is as adequate to a form of a surface to be processed as to provide the necessary degree of uniformity of action of an external ultrasonic field.

Calculations of this type result in that the optimum form of the radiating surface should have a curvature corresponding to that of the irradiated surface.

This principle is true for description of a form of a radiating surface of an operating member intended to irradiate both external surface of a body and internal organs and surfaces of tubular organs.

In particular, it was shown that, to irradiate internal surfaces of tubular organs, for example rectum, it is desirable to have an ellipsoid form of the radiating surface of an operating body; therefore, an operating member having an ellipsoid surface can be effectively and successively used in proctologic practice; in gynaecology, it is best to use an operating member having a radiating surface that is made as a cylinder having a skewed end face portion; in otolaryngology, it is best to use an operating member having a radiating surface that is made as a concave bowl.

Of course, said forms do not limit the assortment of operating members intended to solve different particular problems, and a form of their radiating surfaces can be designed on the basis of the principles stated above.

To practise the inventive method, it is possible to use a device comprising at least a ultrasonic oscillation generator capable of forming a field having a frequency of from 20 to 30 kHz, a liquid phase supply system that provides a hydrodynamic operation mode, and an operating member creating a uniform ultrasonic field evenly acting to a biological material.

It is natural, however, that use of automated systems holds the more promise, and a device to implement the inventive method is equipped therewith.

The device that could implement the described method is shown in drawings where FIG. 1 is a block diagram of the inventive device for therapeutic action with a ultrasonic field to biological tissues. Said device comprises a ultrasonic oscillation generator 1, an acoustic assembly 2 and a ultrasonic tool 3. The acoustic assembly is a half- or full-wave oscillatory system whose principle of operation is based on the magnetostrictive or piezoelectric effects. The ultrasonic tool 3 is a replaceable operating member that helps to effect a direct action to a biological object 4.

The inventive device further comprises a cell membrane resonance frequency sensor 5, a controller 6 and a computer 7. Information about processes taking place in a zone of ultrasonic action to a biological tissue, from the sensor 5 arrives at the controller 6 where it is converted into a signal convenient to be processed by the computer 7. The computer 7 controls the process of action with a ultrasonic field to biological tissues in an automatic mode.

FIG. 2 is a structure diagram of a ultrasonic apparatus that comprises the generator 1, the acoustic assembly 2 and the ultrasonic tool 3 having an operating end 8.

FIG. 3 and FIG. 4 are embodiments of supplying a liquid to a zone of action. In the first embodiment (FIG. 3), the liquid admits at the zone of action through a channel 3 within the body of the tool itself; in the second embodiment (FIG. 4), the liquid admits by means of a special chamber 10 into which the operating end 8 of the ultrasonic tool 3 is placed.

FIGS. 5 to 9 are embodiments of the operating end 8 of the ultrasonic tool 3. The form of the operating end 8 of the ultrasonic tool 3 depends upon a type of biological tissue as well as a form and geometrical parameters of organs to be subjected to the ultrasonic action.

In other words, the form of the operating end of the ultrasonic tool depends directly upon a biological surface to be irradiated by said end.

Figure 6:
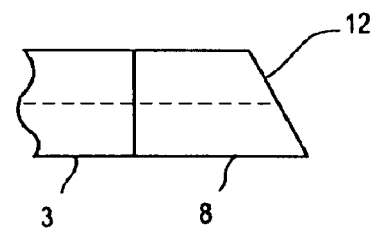
FIG. 6 is a cross-sectional view of a fourth embodiment of the operating end of the present invention shown in relationship to the zone of action.
Figure 7:
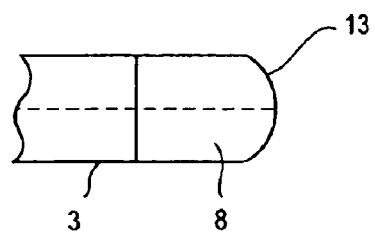
FIG. 7 is a cross-sectional view of a fifth embodiment of the operating end of the present invention shown in relationship to the zone of action.
Figure 8:
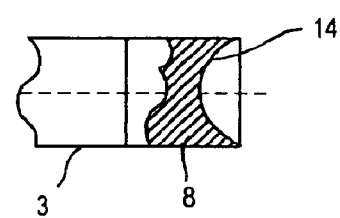
FIG. 8 is a cross-sectional view (showing partial cut-away view) of a sixth embodiment of the operating end of the present invention shown in relationship to the zone of action.
Figure 9:
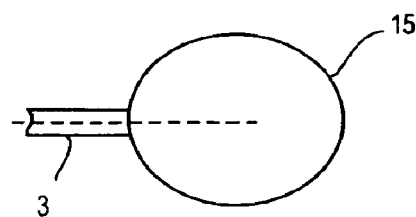
FIG. 9 is a cross-sectional view of a ninth embodiment of the operating end of the present invention shown in relationship to the zone of action.

Thus, the operating end 8 of the ultrasonic tool 3, intended to process:

cavities having a small curvature of surface, including wound surfaces, is made as a cylinder having a flat end face surface 11 (FIG. 5);

hollow organs (vagina, uterus, stomach, etc.), is made as a cylinder having a skewed end face surface 12 (FIG. 6);

cavities having a large curvature of surface, is made as a cylinder having a spherical end face surface 13 (FIG. 7);

organs having a small curvature of surface (tonsils or like), is made as a concave bowl 14 (FIG. 8);

tubular organs (bowels), is made as an ellipsoid 15 (FIG. 9).

Two embodiments of operation of the inventive device are possible.

In first embodiment of operation, the inventive device functions at a fixed frequency of an active ultrasonic field, said frequency corresponding to one of intrinsic frequencies of mechanical oscillations of a cell membrane. Using the computer 7, information is derived about recommended modes of action (a field frequency and intensity, a duration of action), said information taking into account a particular case of medicinal action (the type of a biological tissue, its localisation, the nature and depth of pathology, and so on). Information from the computer 7 arrives at the generator 1 where an electric signal of a resonance frequency having predetermined parameters is formed. The electrical signal formed in the generator 1 through an electrical communication channel arrives at the acoustic assembly 2 where said signal is transformed into mechanical oscillations of a predetermined frequency, that through a mechanical communication channel arrive at the ultrasonic tool 3 where the final formation of the mechanical oscillations having the resonance frequency, takes place up to a programmed level of an intensity of the ultrasonic field. The ultrasonic tool 3 via the operating end 8 acts to the biological object 4 in a membrane-non-destructive hydrodynamic mode. Information about processes taking place in a zone of action of the acoustic tool 3 to the biological object 4, arrives at the sensor 5 and further at the controller 6 where it is converted into a signal convenient to be processed in the computer 7. Based on information arrived from the zone of ultrasonic action, the computer, in the automatic mode, corrects the operating mode of the ultrasonic generator.

In the second embodiment, the device operates in a cell membrane resonance frequency search mode. In case if reliable information about the biological object 4 is absent, the cell membrane resonance frequency is searched using the ultrasonic apparatus.

By means of the computer 7, a frequency range is predetermined that can correspond by resonance frequencies to the biological object 4. Oscillations in the predetermined frequency range are formed in the generator 1 and then, through communication channels "generator—acoustic assembly—ultrasonic tool", are supplied to the biological object, thereby exciting the mechanical oscillations of biological structures at different organisation levels, including a cell level. Information about an oscillation mode of the biological structures, through communication channels "sensor—controller—computer", arrives at the computer 7 where the oscillation mode of the biological structures is estimated for correspondence with the mode of resonance frequencies of membranes. In the automatic mode, the frequency range search continues until the range of cell membrane resonance frequencies is found for a given biological object. Upon determination of the range of resonance frequencies, the device automatically goes to the mode of action to the biological object in accordance with the first embodiment.

The essence of the invention is illustrated by the following Example that has no limiting nature.

EXAMPLE

The patient M., 55 years old. Was delivered with complicated haemorrhoid of external rhonal veins and thrombosis of piles without necrosis.

As a method of treatment, it was selected a ultrasonic action to the mucous coat of rectum, effected in a hydrodynamic mode.

Prior to each procedure, the operative field was preliminary disinfected with the 5% iodopyrone solution or 70% alcohol solution.

There was treatment of piles by insonifying the zone of actions with the ultrasonic field in the hydrodynamic mode. Hydrodynamic conditions were created by supplying the 5% iodopyrone solution through a channel within the body of ultrasonic tool into the sone of action. The frequency of the active ultrasonic field was equal to 23 kHZ and the duration of action was 30 seconds.

When treatment was completed, the heparin ointment was applied onto the treated region, and the surface was insonified in contact with the ultrasonic tool having the ellipsoid operating end.

In this case, hydrodynamic conditions were provided by a hydrophilic base of the ointment used.

The amplitude of oscillations of the active ultrasonic field was within from 40 to 20 microns, and the computer probe has supported that said values produce a resonance response of cell membranes. The insonifying time was from 30 to 60 seconds.

Altogether there were 10 procedures performed every day.

In the process of treatment, improvement of the general state of health was noted already after the first procedures, pains were reduced and then disappeared at all. The patient was discharged in the satisfactory state.

What is claimed is:

1. A method for therapeutic action with a ultrasonic field to biological tissues having the steps of:

transmitting a generated ultrasonic energy into a zone of action;

effecting the action with the ultrasonic field having a frequency corresponding to one of intrinsic mechanical frequencies of a cell membrane;

providing the action in a membrane-non-destructive mode; and providing the action in a hydrodynamic mode.

2. A method according to claim 1 wherein, the action is effected with the ultrasonic field having a frequency of from 23 to 27 kHz and an intensity of from 0.2 to 0.5 mW/cm$^2$.

3. The method according to claim 1 wherein the amplitude of oscillations of the active ultrasonic field is from 40 to 20 microns.

4. The method according to claim 1 wherein the generated ultrasonic energy is transmitted for a time period from 30 to 60 seconds.

* * * * *